US006994551B2

(12) United States Patent
Wang et al.

(10) Patent No.: US 6,994,551 B2
(45) Date of Patent: Feb. 7, 2006

(54) STABLE SELF-ETCHING PRIMER AND ADHESIVE BONDING RESIN COMPOSITIONS, SYSTEMS, AND METHODS

(75) Inventors: Yantong J. Wang, Lyle, IL (US); Byoung I. Suh, Oak Brook, IL (US); Martin Hamer, Skokie, IL (US); Louis J. Sharp, Libertyville, IL (US); Aleksandra Strukowska, Bartlett, IL (US)

(73) Assignee: Bisco, Inc., Schaumburg, IL (US)

( * ) Notice: Subject to any disclaimer, the term of this patent is extended or adjusted under 35 U.S.C. 154(b) by 0 days.

(21) Appl. No.: 10/248,768

(22) Filed: Feb. 14, 2003

(65) Prior Publication Data
US 2003/0171450 A1 Sep. 11, 2003

Related U.S. Application Data

(63) Continuation-in-part of application No. 10/075,751, filed on Feb. 14, 2002.

(51) Int. Cl.
*A61C 5/04* (2006.01)

(52) U.S. Cl. ...................................... 433/226; 523/118
(58) Field of Classification Search ................ 433/226, 433/228.1, 216, 215; 523/115, 116, 118
See application file for complete search history.

(56) References Cited

U.S. PATENT DOCUMENTS

| 4,514,527 A | 4/1985 | Bowen ........................ 523/115 |
| 4,544,467 A | 10/1985 | Bunker et al. .......... 204/159.24 |
| 4,551,550 A | 11/1985 | Bey ............................ 564/215 |
| 4,558,756 A | 12/1985 | Seed .......................... 177/211 |
| 4,640,936 A | 2/1987 | Janda et al. .................. 522/14 |
| 4,657,941 A | 4/1987 | Blackwell et al. ............ 522/14 |
| 4,659,751 A | 4/1987 | Bowen ....................... 523/116 |
| 4,816,495 A | 3/1989 | Blackwell et al. ............ 522/14 |
| 4,966,934 A | 10/1990 | Huang et al. ................ 524/315 |
| 5,264,513 A | 11/1993 | Ikemura et al. ............. 526/318 |
| 5,270,351 A | 12/1993 | Bowen ....................... 523/116 |
| 5,304,585 A | 4/1994 | Bunker ....................... 523/116 |
| 5,320,886 A | 6/1994 | Bowen ....................... 428/34.1 |
| 5,348,988 A | 9/1994 | Suh et al. ................... 523/118 |
| 5,658,963 A | 8/1997 | Qian et al. .................... 522/14 |
| 5,834,532 A | 11/1998 | Yamamoto et al. ......... 523/118 |
| 5,925,690 A * | 7/1999 | Fuchigami et al. ......... 523/118 |
| 6,245,872 B1 | 6/2001 | Frey et al. .................. 526/277 |
| 6,592,372 B2 * | 7/2003 | Jia et al. ..................... 433/215 |
| 2002/0019456 A1 | 2/2002 | Jia ............................. 523/115 |

FOREIGN PATENT DOCUMENTS

EP 0705 590 A1 10/1996

* cited by examiner

*Primary Examiner*—Melba N. Bumgarner
(74) *Attorney, Agent, or Firm*—Ice Miller

(57) ABSTRACT

Stable self-etching copolymerizable primer compositions are provided including compounds having a polymerizable ethylenically unsaturated groups and acidic groups, and optionally comonomers and suitable solvents. Such compositions are used in conjunction with dental adhesives to provide one or multi-component dental systems capable of etching or decalcifying tooth dentin and enamel without the need for a separate rinse step. Methods of use of such compositions according to the present invention include application for priming and imparting enhanced adhesion between the primers, adhesives, and the tooth substrates such as dentin or cut or uncut enamel, and subsequently applied dental composites, restoratives or other dental components.

2 Claims, 17 Drawing Sheets

Fig. 1 Dentin sanded by 320# Grit paper
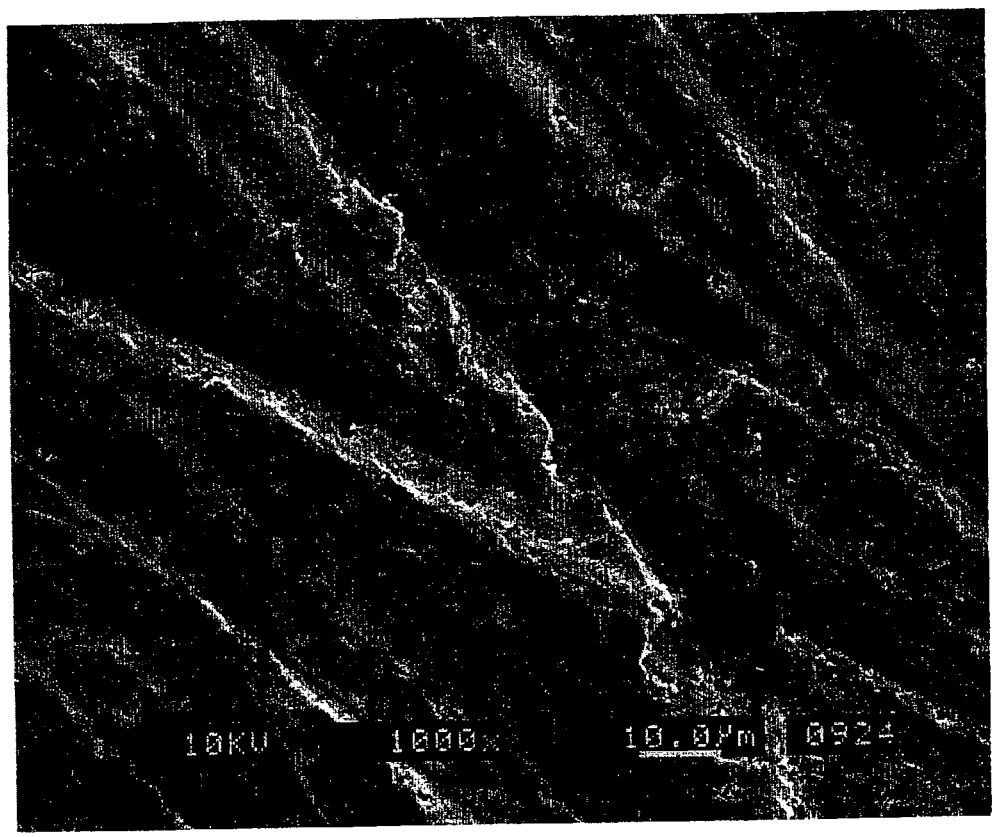

Fig. 2 Dentin etched by Etch-37 (37% H3PO4) for 15s
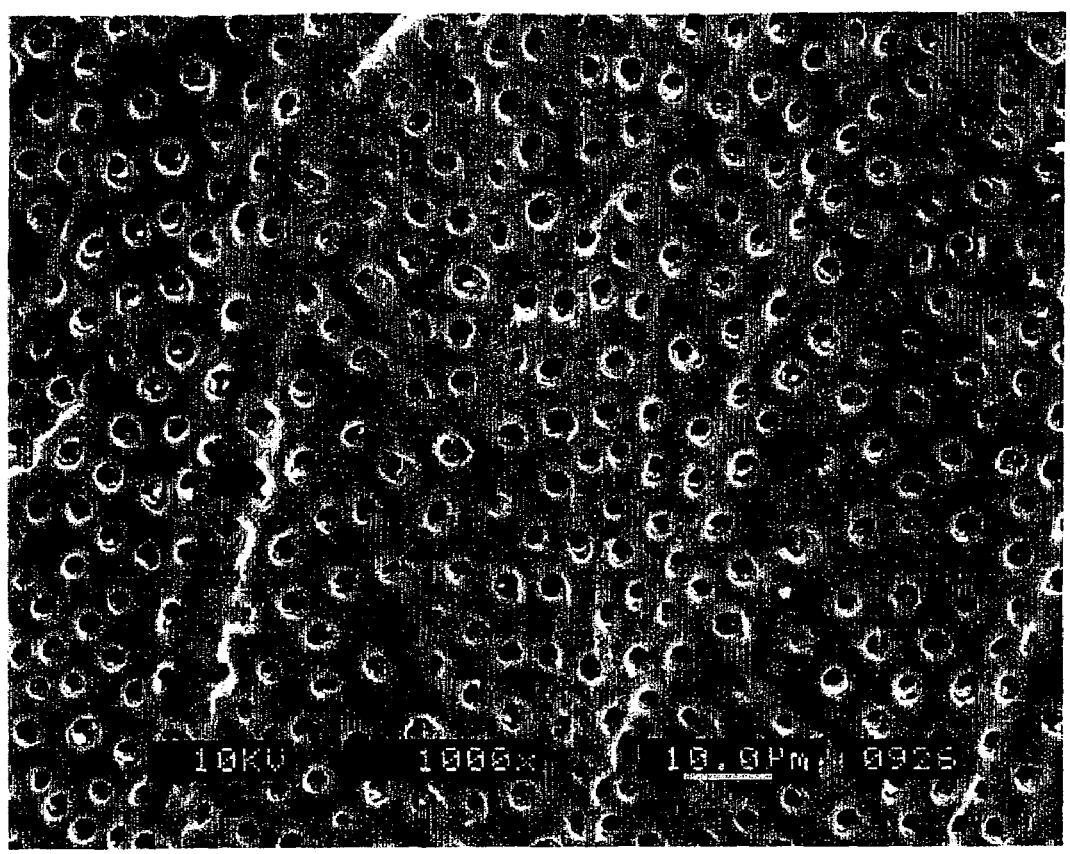

Fig. 3  320 paper sanded dentin etched by 30/10 AMPS/Bis-MEP for 10s with agitation
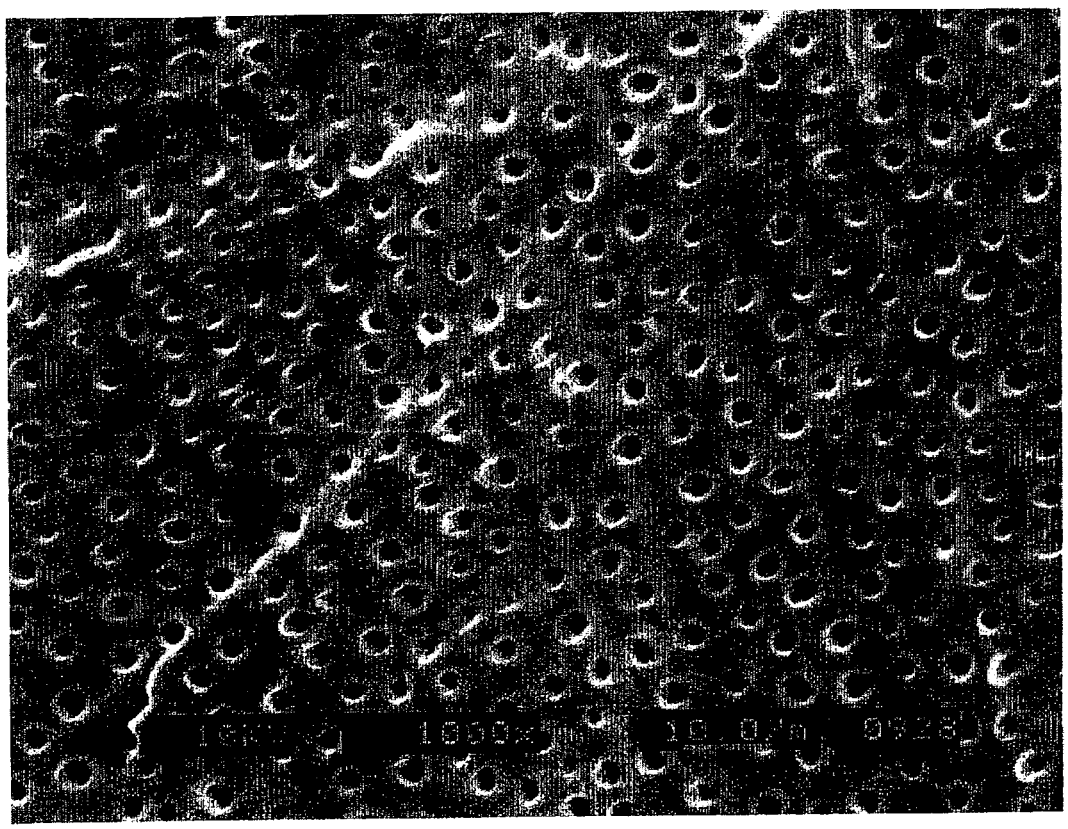

Fig. 4 320 paper sanded dentin etched by 40/10 AMPS/Bis-MEP for 10s with agitation
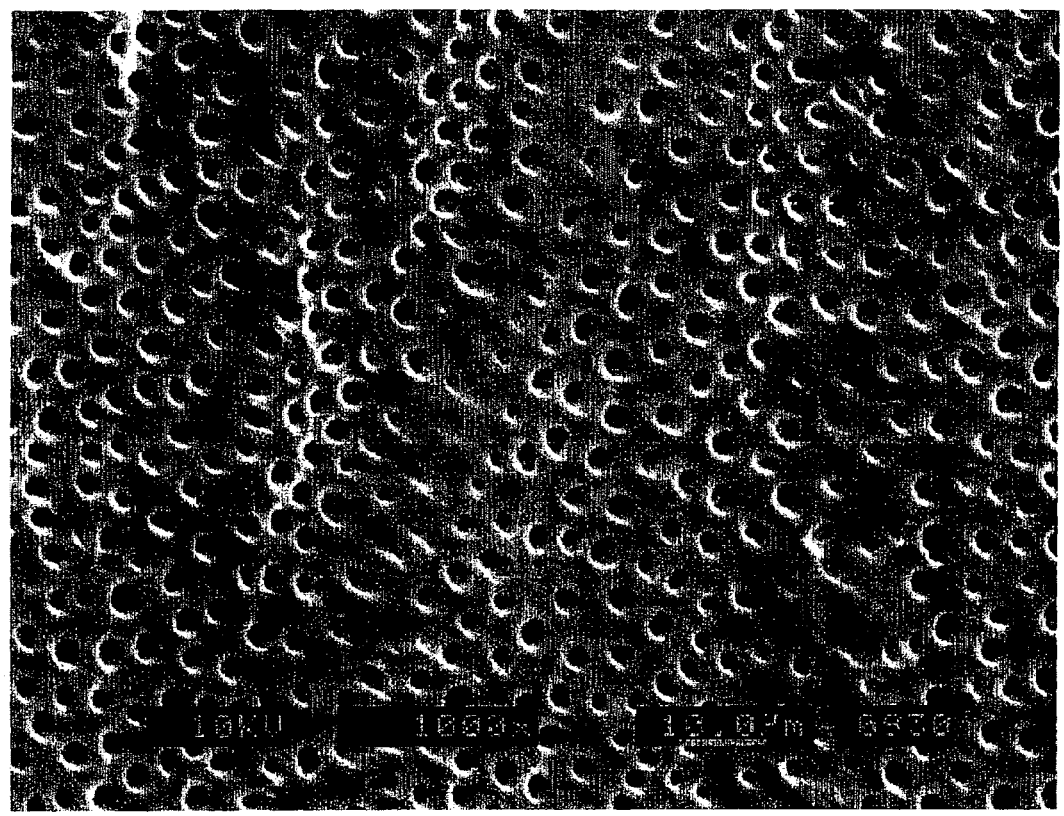

Fig. 5 Enamel sanded by 320 Grit paper

Fig. 6 Enamel sanded by 320 Grit paper and then etched by Etch-37 (37% H3PO4) for 15s
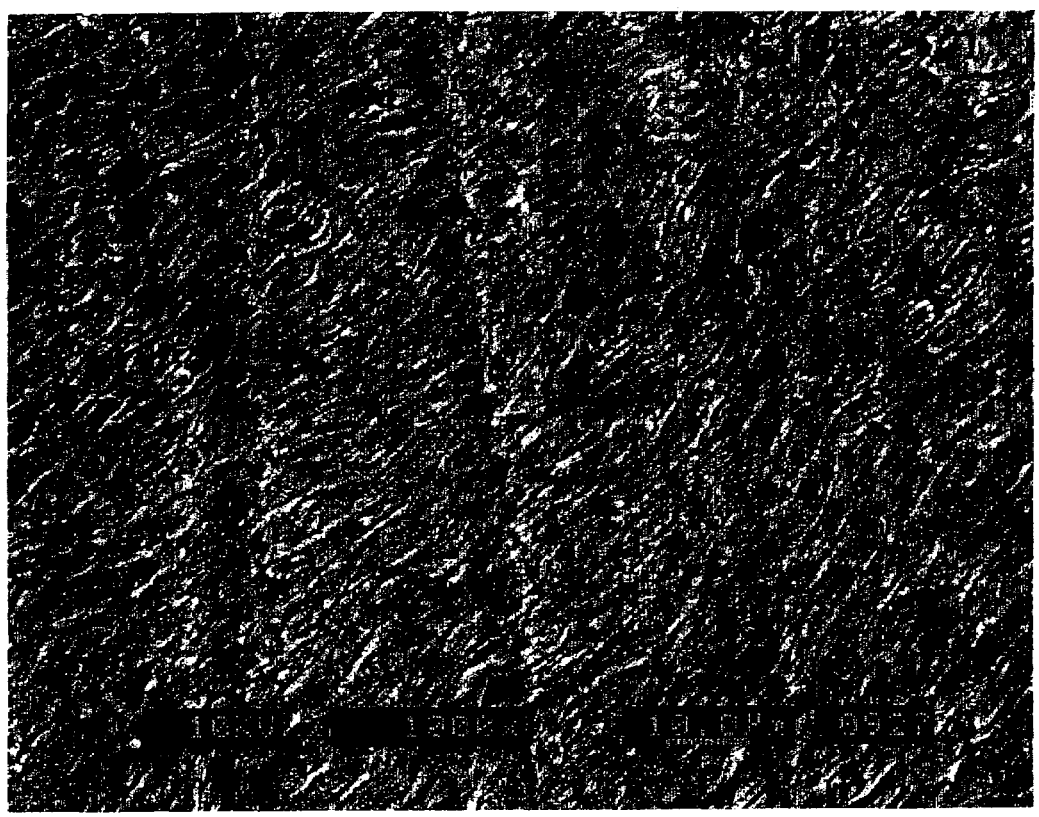

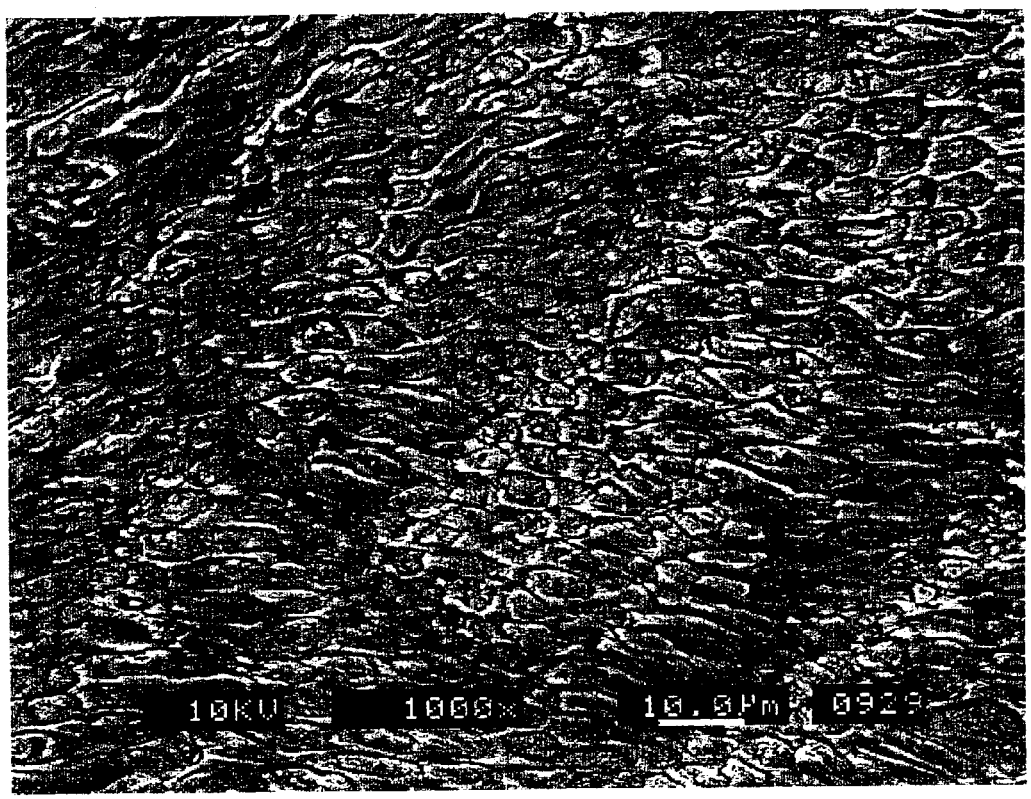
Fig. 7 320 paper sanded enamel etched by 30/10 AMPS/Bis-MPE for 10s with agitation Fig. 8 320 paper sanded enamel etched by 40/10 AMPS/Bis-MEP for 10s with agitation
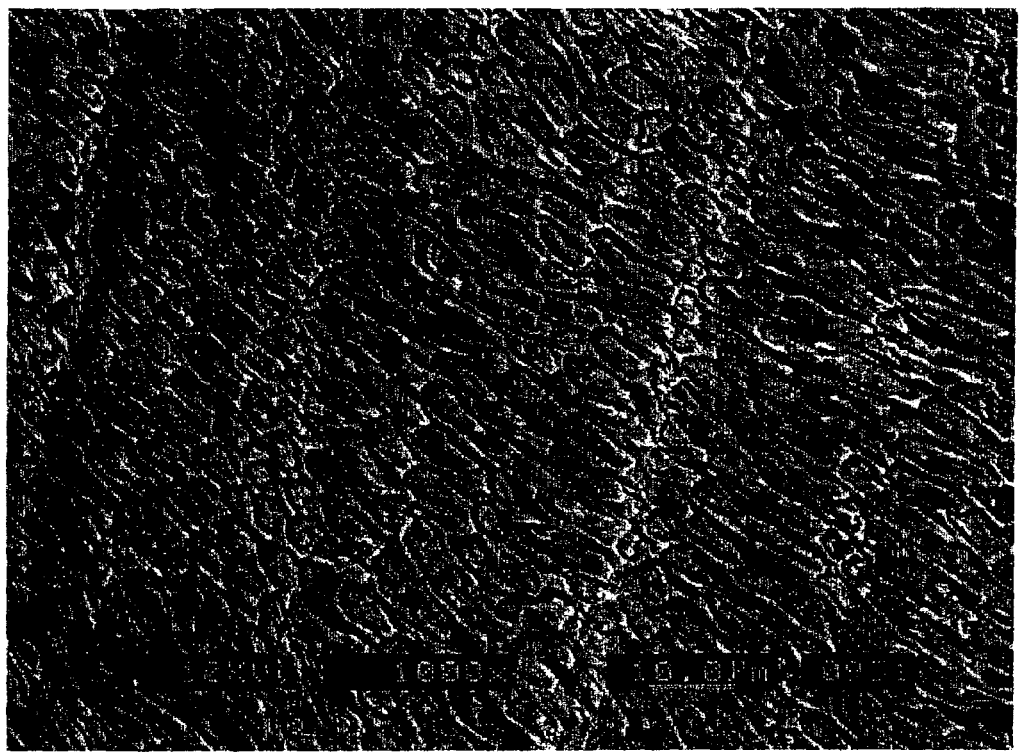

Fig. 9 Uncut pumiced enamel
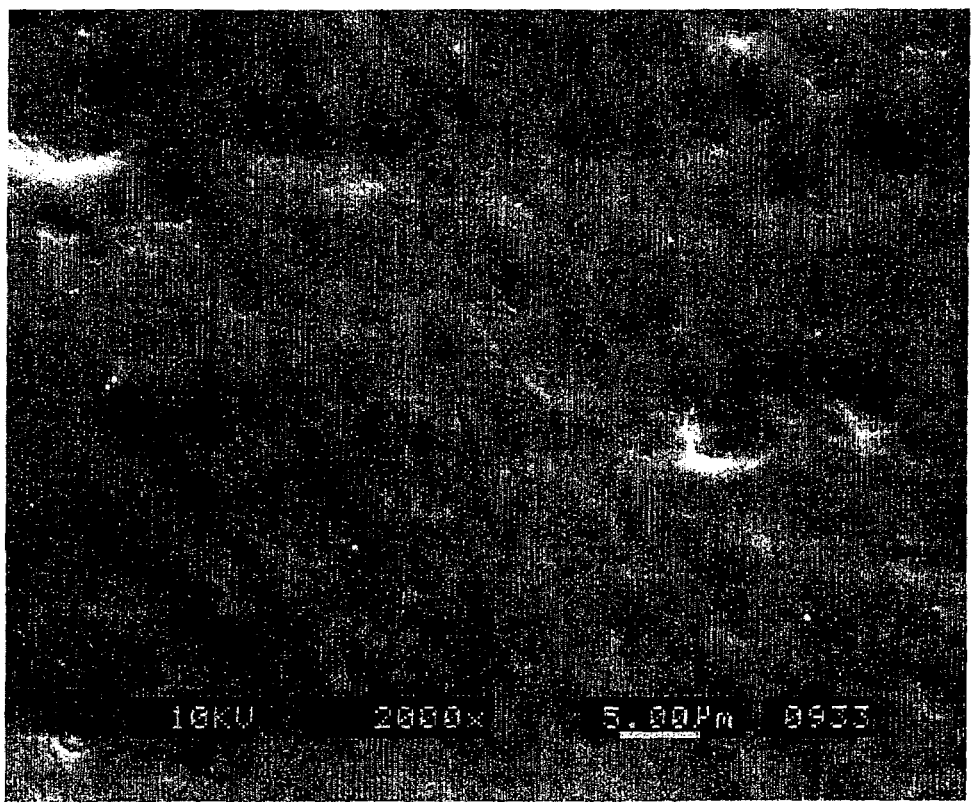

Fig. 10 Uncut pumiced enamel etched by Etch-37 (37%H3PO4) for 15s
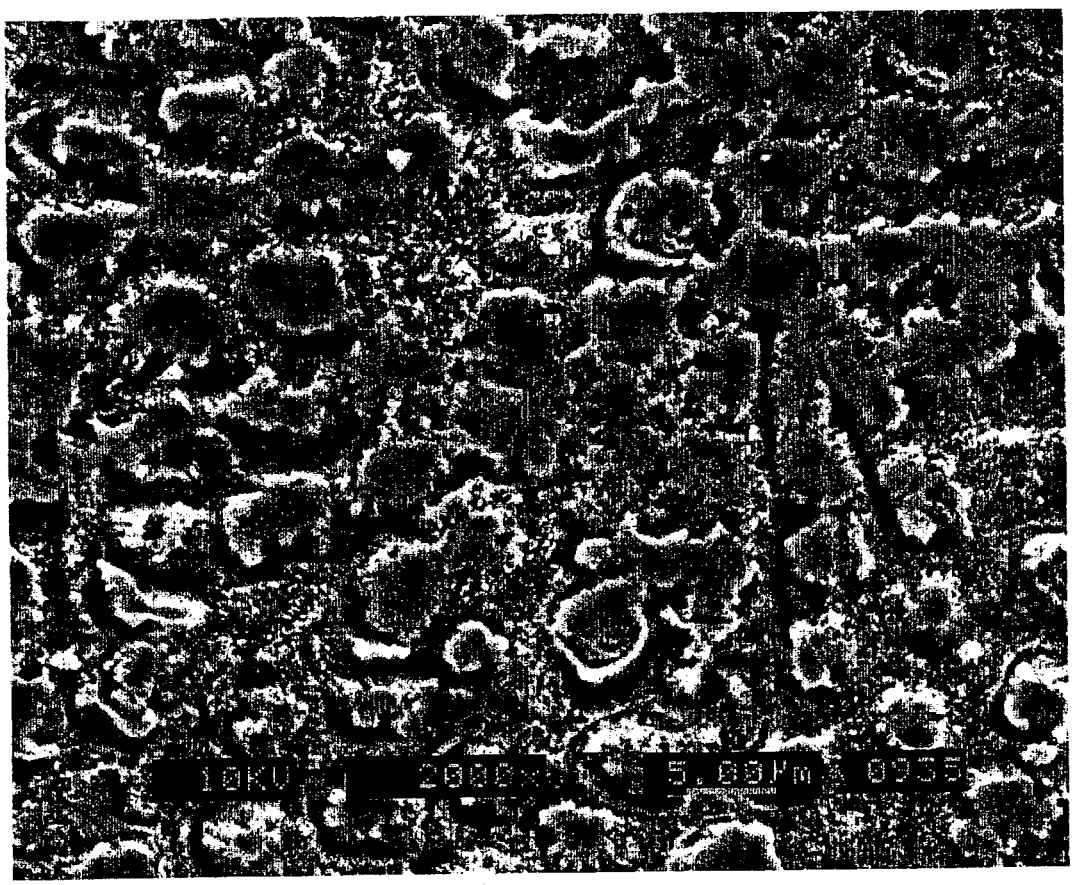

Fig. 11 Uncut pumiced enamel etched by 30/10 Bis-MEP for 10s with agitation
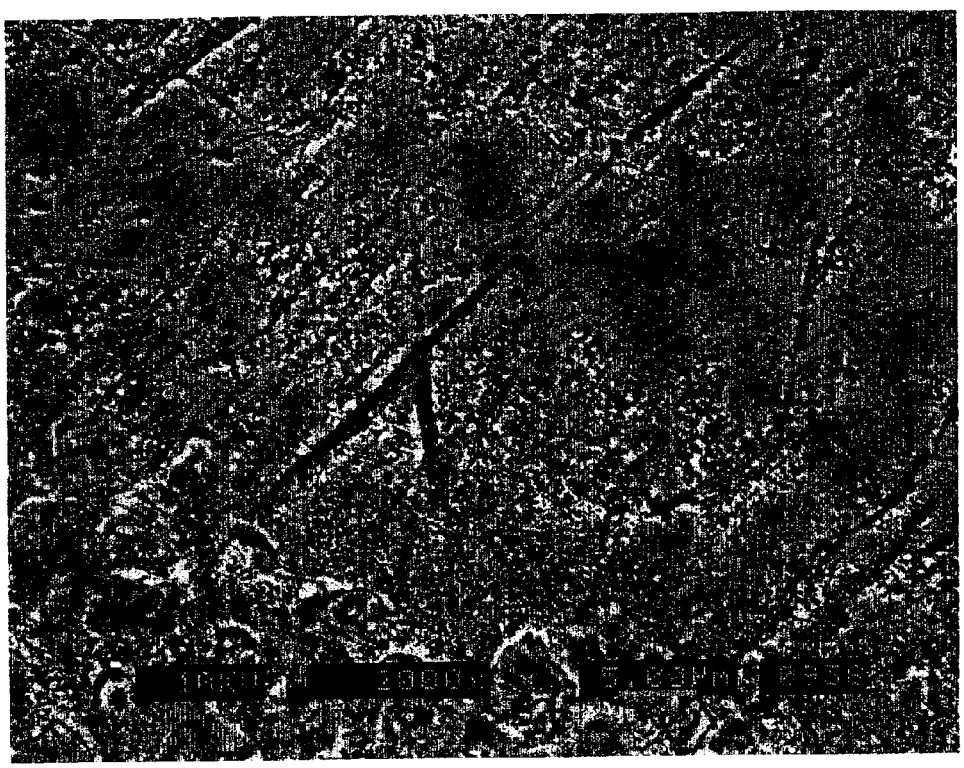

Fig. 12 Uncut pumiced enamel etched by 38/10 AMPS/Bis-MEP for 10s with agitation
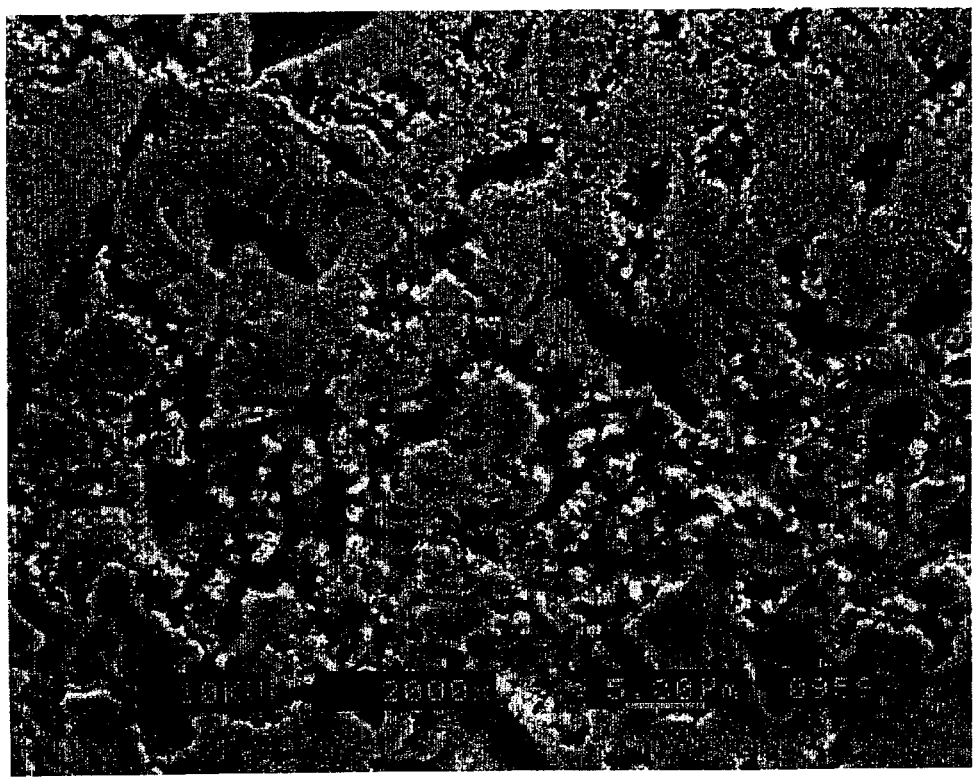

Fig. 13 Uncut pumiced enamel etched by 40/10 AMPS/Bis-MEP for 10s with agitation
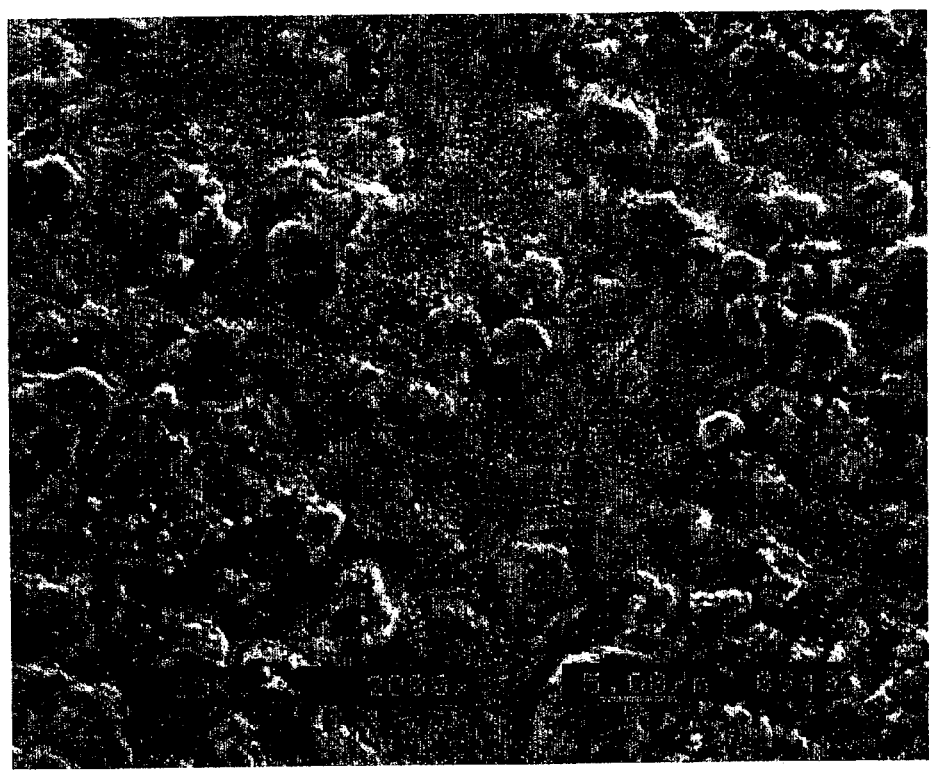

Fig. 14 Cross bur cut enamel
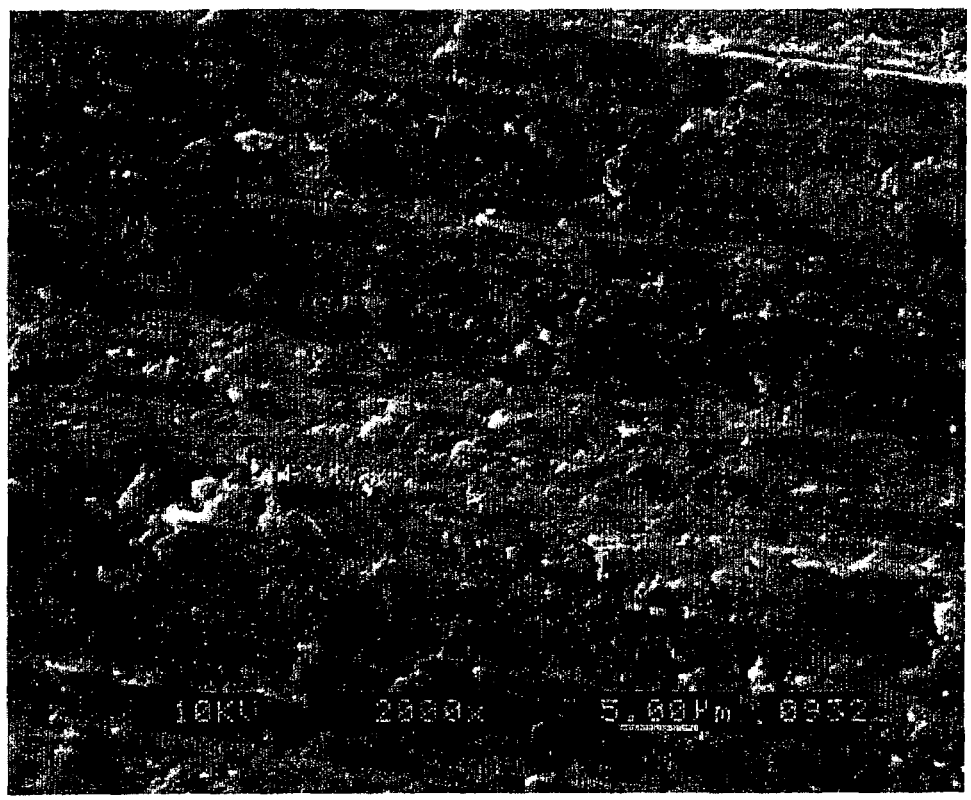

Fig. 15 Cross bur cut enamel etched by Etch-37 (37%H3PO4) for 15s

Fig. 16 Cross bur cut enamel etched by 30/10 AMPS/bis-MEP for 10s with agitation
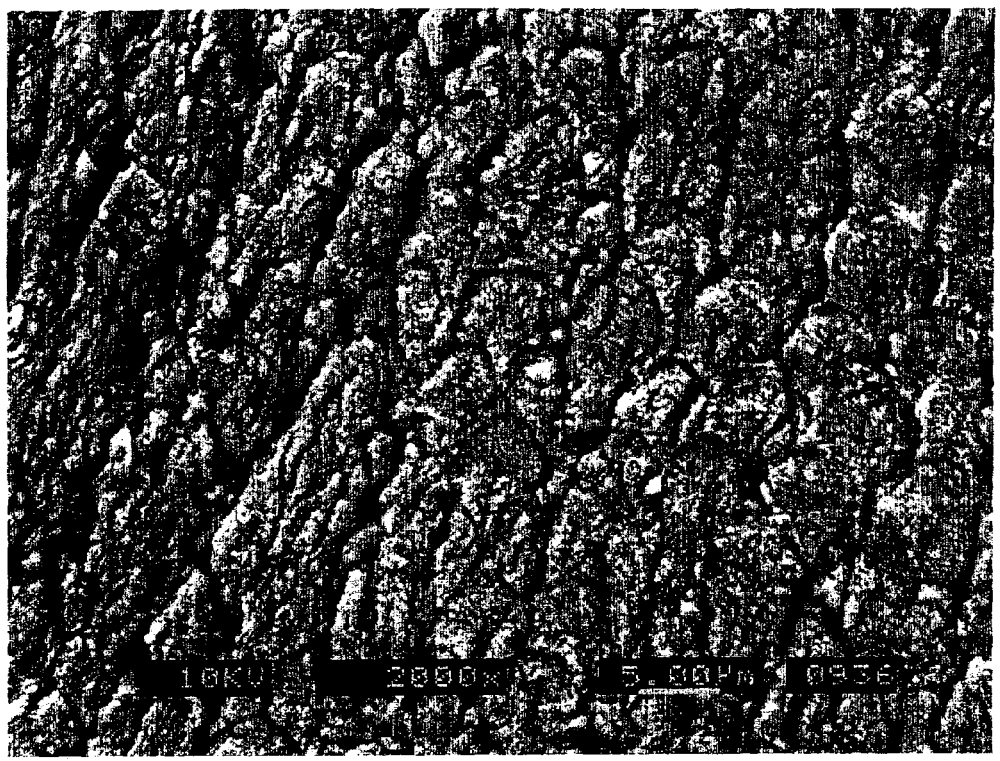

Fig. 17 Cross bur cut enamel etched by 40/10 AMPS/Bis-MEP for 10s with agitation

STABLE SELF-ETCHING PRIMER AND ADHESIVE BONDING RESIN COMPOSITIONS, SYSTEMS, AND METHODS

CROSS REFERENCE TO RELATED APPLICATIONS

The present application is a continuation-in-part of co-pending U.S. patent application Ser. No. 10/075,751, filed Feb. 14, 2002, the contents of which are incorporated herein by reference.

BACKGROUND OF INVENTION

1. Field of the Invention

The present invention relates generally to etchants, primers and adhesive bonding systems and methods. More specifically, the present invention relates to primer compositions that are self-etching, and to simplified adhesive bonding systems using such compositions. The compositions and methods of the present invention enhance the bonding of dental adhesives, composites, and other dental prostheses to dentin, enamel and tooth tissue.

2. Background of the Invention

Recent advances in dental restorative techniques include the use of materials such as composite resins to effect tooth filling and restoration instead of metal amalgams. Other advances include the use of new dental components such as thin wire braces and other types of dental components made of metal, ceramics, resins or other bio-compatible substances. Depending on the clinical picture, such restoratives and components may need to be applied directly to the tooth dentin and/or enamel, or may need to be applied to other bio-compatible substrates such as metals, ceramics, resins or amalgams which may already exist in the patient and/or are to be added as part of the clinical treatment.

Common to the foregoing techniques, and many older forms of dental restorative techniques, is the general need for dental restorative techniques using etchants and primers which are simple to use. Ideally, the dental professional would use the etching, priming, and adhesive bonding systems in a manner that requires a minimum of time for the patient in the chair. In addition, such ideal etching, priming, and adhesive bonding systems would also provide bond strengths of the restorative or other dental component to the chosen dental substrate which approach the strength of the underlying substrates.

Several primer and adhesive bonding systems have been reported in the literature which have achieved some, but not all of the above-stated goals. A general discussion of multiple-component primer and adhesive bonding systems and their predecessors is set out in Suh, "I-Bond—Fourth Generation Dentin Bonding System," J. Esthetic Dentistry, Vol. 3, No. 4, pp. 139–147 (July–August, 1991) and in Bowen U.S. Pat. No. 5,270,351 at Col. 1, lines 29-Col. 2, line 36 and Col. 2, lines 54–64, the disclosures of which are hereby incorporated by reference. "One-component" dental primer and adhesive bonding systems are generally disclosed in, for example, Blackwell et al. U.S. Pat. Nos. 4,657,941 and 4,816,495 and Huang et al. U.S. Pat. No. 4,966,934 all of which are assigned to Dentsply Research and Development Corporation (hereinafter also collectively referred to as the Dentsply patents), Bunker U.S. Pat. No. 5,304,585, which is assigned to 3M, and Suh et. al. U.S. Pat. No. 5,658,963, which is assigned to Bisco, Inc.

All of these etchant, primer and adhesive bonding systems generally require a first pretreatment step of the dental substrate with mordants and/or acidic solutions to decalcify and remove the smear layer and to etch tooth dentin and/or enamel before application of the dental adhesive, dental restorative or other component. This is generally referred to as the "bonding technique" because the dental restorative is applied to the dental substrate while it is still wet after rinsing with water to remove the etchant and/or primer solution. To further enhance bonding between the substrate and the multi-component dental restorative some of these systems also employ at least two additional primer or adhesive enhancing or bonding compounds which must either (1) be applied separately and sequentially to the dental substrate, (2) must be mixed together by the dental professional in the office immediately before use on the patient to prevent premature polymerization of the components (for example see Bowen U.S. Pat. Nos. 4,514,527; 4,551,550; 4,558,756, 4,659,751; 5,320,886; and 5,270,351; Suh U.S. Pat. No. 5,348,988; and Bunker U.S. Pat. No. 4,544,467; the disclosures of which are hereby incorporated by reference). Such multi-component/multi-step methods necessarily require the dental professional to perform an initial etching step followed by a separate rinsing step as well as a step of admixing of primers and/or primers and initiator while the patient waits in the chair, unnecessarily complicating the overall restorative process and increasing the treatment time for the patient. Moreover such systems generally require the use of an additional component, an adhesive bonding resin, applied as an additional step in the process in order to achieve such high bond strengths, further complicating the restorative process. Even the use of "one-component" dental primer and adhesive bonding systems on tooth dentin and/or enamel substrates is still often preceded by an initial pre-treatment step of "etching" or decalcifying the dental substrate with an acidic solution followed by rinsing step(s) to remove most or all of the etchant composition and subsequently followed by application and bonding of the dental restorative or luting composite by copolymerization through light-curing or self-curing.

Other commercial self-etching priming systems include Clearfil SE Bond (a/k/a MegaBond, Kuraray Corporation) a two component self-etching primer adhesive system including a methacryloyloxydecyl dihydrogen phosphate (MDP) primer solution and a MDP/bonding resin solution applied sequentially to the tooth surface. SE Bond requires light-curing and cannot be applied to indirect restoration procedures because of the thickness of the film. It also exhibits poor enamel etching, requiring conventional acid etching on uncut enamel. Another light-cure only self-etching adhesive system is Prompt L-Pop sold by ESPE/3M. The manufacturer indicates that this all-in-one self-etching adhesive system contains an organophosphate monomer. Different from SE Bond, this system does not need a priming procedure. The mixture of two components is applied to tooth surfaces right after they are mixed. It also is reported to exhibit poor bonding to tooth enamel and does not bond to self-cure materials.

U.S. Pat. No. 4,640,936 (issued Feb. 3, 1987 to Janda et al.) suggests the preparation and use of a dental composition consisting of a solution of (i) at least one phosphate selected from the group consisting of methacryloyloxyethyl dihydrogen phosphate and bis-(methacryloyloxyethyl) hydrogen phosphate and (ii) a photopolymerization catalyst comprising camphor quinone and an amine, in acetone. The composition is intended to be used with a separate photopolymerizable dental sealing composition.

U.S. Pat. No. 4,719,149 (issued Jan. 12, 1988 to Aasen et al.) describes the use of an acid and a water-soluble film former as a primer for hard tissue. The acid has a pKa less than or equal to that of phenol (i.e. less than or equal to 9.9), and the film former has a solubility in water of at least about 5 weight percent. The acid and film former are applied to the hard tissue either concurrently or sequentially. The primers were suggested as an adhesive for dentin, enamel, and other hard tissues.

U.S. Pat. No. 5,264,513 (issued Nov. 23, 1993 to Ikemura et al.) suggests the preparation of a dental composition containing water, a polymerizable compound having a hydroxyl group, a polymerizable compound having an acidic group, and a curing agent.

U.S. Pat. No. 5,834,532 (issued Nov. 10, 1998 to Yamamoto et al.) describes primer compositions containing a polymerizable monomer containing an acid group and an initiator. The patent further describes curable compositions that are useful for restoring tooth surface material.

U.S. Pat. No. 5,925,690 (issued Jul. 20, 1999 to Fuchigami et al.) describes a dental composition containing a phosphoric acid group-containing monomer, a carboxylic acid groups-containing monomer, and water. The composition provides adhesion to dentin and to enamel.

U.S. Pat. No. 6,245,872 (issued Jun. 12, 2001 to Frey et al.) provides a dental composition containing i) 10 to 90 parts by weight of at least one singly or repeatedly ethylenically unsaturated phosphoric acid ester, ii) 5 to 85 parts by weight of a solvent, iii) 0.01 to 5 parts by weight of an initiator which can form free radicals, and iv) 0 to 10 parts by weight of customary auxiliaries and additives. A tooth is treated with the composition, and immediately is coated with polymerizable filling material.

U.S. Patent Application Publication No. 2002/0019456 A1 (published Feb. 14, 2002 to Jia) suggests a composition comprising a solution of a $SO_3$ terminated compound resin, and an optional fluoride source. The $SO_3$ terminated monomer can include 2-acrylamido-2-methyl-propanesulfonic acid (AMPS), AMPS derivatives, 2-sulfoethyl methacrylate (SEM), SEM derivatives, 3-sulfopropyl methacrylate (SPM), SPM derivatives, or mixtures thereof. The composition is described as a self-etching primer. The compositions contain a solvent that may include water and/or a polar solvent partially or totally soluble in water. Various examples of the composition were presented, but stability data was not disclosed.

There is, therefore, a need in the art for the true self-etchant primer compositions that are capable of etching dentin and enamel in both self-curable and light-curable polymerization systems and can be applied and used without separate rinsing steps and which themselves are polymerizable within the dental curing systems to enhance bonding of the dental adhesive and/or dental restorative material to dentin and enamel and overall, permit a quicker, simpler, and easier restorative process, yet still provide a consistently high and stable bond strength of adhesives, composites, resins, metals and other dental prostheses to dentin, enamel, tooth tissue and to other substrates.

SUMMARY OF INVENTION

In accordance with the present invention, there are provided novel self-etching copolymerizable primer compositions comprising compounds having a polymerizable group or moiety and an acidic group or moiety that permits decalcification of tooth dentin and enamel without substantial interference with polymerization of the other group within self-cure and light-cure dental restorative systems. Preferred compositions according to the present invention include one or more compounds having a polymerizable group or moiety of the general formula, $CH_2{=}CX{-}C(O){-}$, wherein X is hydrogen, methyl or a lower alkyl group, and also having an acidic group or moiety including sulfonic ($-SO_3H$) or phosphoric ($-PO(OH)(OR)$) ($R{=}H$ or alkyl) groups. Presently preferred self-etching compositions include sulfopropyl acrylamide ($CH_2{=}CHCONHC(CH_3)_2CH_2{-}SO_3H$) (2-acrylamido-2-methylpropanesulfonate, AMPS), Bis-[2-(methacryloyloxy)ethyl] phosphate $[CH_2{=}C(CH_3)COCH_2CH_2]_2{-}PO(OH)$ (Bis-MEP), 2-sulfoethyl methacrylate ($CH_2{=}C(CH_3)COOCH_2CH_2{-}SO_3H$) (SEMA), a combination of sulfobenzoic anhydride-hydroxyethylmethacrylate (SBA-HEMA), optionally additional acid(s), optionally additional monomer(s), and a solvent which can be used in conjunction or combination with an adhesive bonding resin component. Preferred self-etching compositions include one or more of these compounds supplied in a single container or in two containers the contents of which are admixed before application to the dental surface. Such novel self-etching primer compositions according to the present invention, explained in more detail below, promote adhesion between a dental substrate such as dentin or enamel and a dental adhesive, and subsequently applied dental restorative materials, composites or other dental devices in direct and indirect dental techniques employing light-cure and self-cure polymerization protocols. Methods according to the present invention include use of the foregoing novel compositions as a single step for etching and priming and imparting enhanced adhesion between dental substrates and dental adhesives without the need for separate rinsing steps or etching and priming steps.

Compositions and methods according to the present invention provide for etching of tooth dentin and enamel substrates while providing consistently high bonding strengths between the substrate and adhesives, restoratives or devices. In addition the compositions and methods according to the present invention allow light-curing or self-curing of these self-etching copolymerizable primer compositions with an applied dental adhesive and subsequent application of a self-cure, light-cure or dual-cure composite restorative compositions or other dental materials capable of bonding with the primer and adhesive. Certain of the preferred compositions and methods of the present invention exhibit high bond strengths even when packaged together in a single solution and stored over considerable periods of time, permitting formulation of the compositions well in advance of the time of their intended application. The compositions can further comprise one or more antimicrobial agents. It is further preferable that the inventive compositions be stable at room temperature (e.g. at 22° C.) to provide long shelf life for dental kits or systems employing such compositions.

Other objects and advantages of the invention will be apparent to those skilled in the art from the following detailed description, taken in conjunction with the appended claims.

BRIEF DESCRIPTION OF THE DRAWINGS

FIG. 1 is a SEM (taken at 1000× magnification) of the dentin surface of a human tooth after sanding with 320 grit paper before application of an etchant.

FIG. 2 is a SEM (taken at 1000× magnification) of the dentin surface of a human tooth sanded as described in reference to FIG. 1 above and after application of a conventional 37% phosphoric acid etchant for 15 sec. and rinsing.

FIG. 3 is a SEM (taken at 1000× magnification) of the dentin surface of a human tooth sanded as described in reference to FIG. 1 above and after application of a self-etching copolymerizable primer composition with Primer B comprising 30 wt. % AMPS and 10 wt. % Bis-MEP for 10 sec. with agitation and rinsing.

FIG. 4 is a SEM (taken at 1000× magnification) of the dentin surface of a human tooth sanded as described in reference to FIG. 1 above and after application of a self-etching copolymerizable primer composition with Primer B comprising 40 wt. % AMPS and 10 wt. % Bis-MEP for 10 sec. with agitation and rinsing.

FIG. 5 is a SEM (taken at 1000× magnification) of the enamel surface of a human tooth sanded with 320 grit paper before application of an etchant.

FIG. 6 is a SEM (taken at 1000× magnification) of the enamel surface of a human tooth sanded as described in reference to FIG. 5 above and after application of a conventional 37% phosphoric acid etchant for 15 sec. and rinsing.

FIG. 7 is a SEM (taken at 1000× magnification) of the enamel surface of a human tooth sanded as described in reference to FIG. 5 above and after application of a self-etching copolymerizable primer composition with Primer B comprising 30 wt. % AMPS and 10 wt. % Bis-MEP for 10 sec. with agitation and rinsing.

FIG. 8 is a SEM (taken at 1000× magnification) of the enamel surface of a human tooth sanded as described in reference to FIG. 5 above and after application of a self-etching copolymerizable primer composition with Primer B comprising 40 wt. % AMPS and 10 wt. % Bis-MEP for 10 sec. with agitation and rinsing.

FIG. 9 is a SEM (taken at 2000× magnification) of the surface of uncut pumiced human tooth enamel before application of an etchant.

FIG. 10 is a SEM (taken at 2000× magnification) of the enamel surface of a human tooth pumiced as described in reference to FIG. 9 above and after application of a conventional 37% phosphoric acid etchant for 15 sec. and rinsing.

FIG. 11 is a SEM (taken at 2000× magnification) of the enamel surface of a human tooth pumiced as described in reference to FIG. 9 above and after application of a self-etching copolymerizable primer with Primer B composition comprising 30 wt. % AMPS and 10 wt. % Bis-MEP for 10 sec. with agitation and rinsing.

FIG. 12 is a SEM (taken at 2000× magnification) of the enamel surface of a human tooth pumiced as described in reference to FIG. 9 above and after application of a self-etching copolymerizable primer composition with Primer B comprising 38 wt. % AMPS and 10 wt. % Bis-MEP for 10 sec. with agitation and rinsing.

FIG. 13 is a SEM (taken at 2000× magnification) of the enamel surface of a human tooth pumiced as described in reference to FIG. 9 above and after application of a self-etching copolymerizable primer composition with Primer B comprising 40 wt. % AMPS and 10 wt. % Bis-MEP for 10 sec. with agitation and rinsing.

FIG. 14 is a SEM (taken at 2000× magnification) of the surface of cross burr cut human tooth enamel before application of an etchant.

FIG. 15 is a SEM (taken at 2000× magnification) of the enamel surface of a human tooth cut as described in reference to FIG. 14 above and after application of a conventional 37% phosphoric acid etchant for 15 sec. and rinsing.

FIG. 16 is a SEM (taken at 2000× magnification) of the enamel surface of a human tooth cut as described in reference to FIG. 14 above and after application of a self-etching copolymerizable primer composition with Primer B comprising 30 wt. % AMPS and 10 wt. % Bis-MEP for 10 sec. with agitation and rinsing.

FIG. 17 is a SEM (taken at 2000× magnification) of the enamel surface of a human tooth cut as described in reference to FIG. 14 above and after application of a self-etching copolymerizable primer composition with Primer B comprising 40 wt. % AMPS and 10 wt. % Bis-MEP for 10 sec. with agitation and rinsing.

DETAILED DESCRIPTION

The presently preferred compositions of the present invention comprise self-etching copolymerizable primer compositions containing one or more compounds having (a) an ethylenically unsaturated polymerizable group or moiety of the general formula $CH_2=CX-C(O)-$ wherein X is hydrogen, methyl or a lower alkyl group, and also having an acidic group or moiety including sulfonic ($SO_3H$) or phosphoric (R=H or alkyl) groups. Presently preferred self-etching compositions include sulfopropyl acrylamide ($CH_2=CHCONHC(CH_3)_2CH_2-SO_3H$) (2-acrylamido-2-methylpropanesulfonate, AMPS), Bis-[2-(methacryloyloxy)ethyl]phosphate ($(CH_2C(CH_3)COCH_2CH_2)_2-PO(OH)$ (Bis-MEP), 2-sulfoethyl methacrylate ($CH_2=C(CH_3)COOCH_2CH_2-SO_3H$) (SEMA), and the polymerizable, hydrophilic, self-etching primer monomer sulfobenzoic anhydride-hydroxyethylmethacrylate (SBA-HEMA), which is the reaction product of sulfobenzoic anhydride (SBA) with 2-hydroxyethyl methacrylate (2-HEMA) (b) optionally an additional monomer; (c) optionally an acid; and (d) a solvent. According to certain preferred embodiments of the invention, the components (a), (b), (c) and (d) are selected so that upon mixing of the components, the substantial polymerization of the resin components (a) and (b) results upon contact of the mixture and a self-cure or activated light-cure polymerization initiator. The structure of SBA-HEMA is set out below.

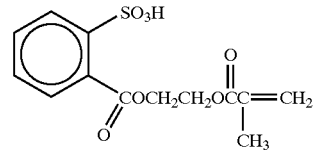

More specifically the self-etching copolymerizable primer compositions according to the invention include a mixture of (a) at least about 0.5 to about 75 wt. % of one or more of the polymerizable self-etching copolymerizable monomer compound(s), more preferably from about 5 to about 70 wt. % and more preferably from about 10 to about 70 wt. % of such compound(s) suspended or dissolved in a suitable solvent.

The solvent can generally be any solvent that dissolves or suspends the self-etching primer monomer(s). The solvent can comprise water, ethanol, acetone, or mixtures thereof. The solvent can be mixtures of two or more solvents. For example, the solvent can be a mixture of water and ethanol, a mixture of water and acetone, a mixture of ethanol and acetone, or a mixture of water, ethanol, and acetone.

Preferred self-etching compositions according to the present invention include compositions in which AMPS, Bis-MEP and/or SEMA monomers are supplied in a first container suspended or dissolved in a suitable solvent, preferably lacking water for improved stability. A second container containing colorant, dye or pH indicator, water and ethanol is also supplied. The contents of these two containers are admixed and the admixture is applied to the tooth structure. Other preferred self-etching compositions include SBA-HEMA supplied in a one component system in a suitable solvent in a single container. Presently preferred self-etching compositions include from about 5 to about 50 wt. % AMPS and from about 5 to about 40 wt. % Bis-MEP suspended and dissolved in a first solvent in a first container, and Thymol blue sodium salt and ethanol in a second container. For example, the containers comprising separate compartments of a two compartment delivery system such as "Dip 'N' Mix" by Dentaco of Bad Homburg, Germany may be used for convenient mixing and dispensing by the dental practitioner. Also presently preferred are self-etching copolymerizable compositions comprising an antimicrobial agent such as benzalkonium chloride (BAC) or chlorhexidine gluconate (CHXG) present in the composition in single component systems or in either or both components of two component systems according to the present invention. For example, BAC in ranges from about 0.01 wt. % to about 0.5 wt. % or chlorhexidine gluconate in ranges from about 0.01 wt. % to about 0.5 wt. % may be added to the compositions.

AMPS (AMPS 2404) was obtained from Lubrizol Corporation (Wickliffe, Ohio). Bis-MEP was obtained from Sigma-Aldrich Chemical Company (Milwaukee, Wis.). SEMA was obtained from Polyscience, Inc. (Warrington, Pa.). SBA-HEMA was made as disclosed below.

Presently preferred optional comonomers according to the present invention include 2-HEMA and other monomers such as hydroxypropyl methacrylate (HPMA) containing one or more functional hydroxy groups and reactive vinyl groups. Such comonomers may be employed to improve handling characteristics of the self-etching copolymerizable composition. The comonomers are preferably present in the composition from about 0.5 wt. % to about 50 wt. %, more preferably from about 1 wt. % to about 30 wt. %, and presently most preferably from about 5 wt. % to about 25 wt. % of the total composition. The preferred concentration of such comonomers depends in part on the particular self-etching copolymerizable monomers selected for use in the invention (AMPS, Bis-MEP, SEMA and/or SBA-HEMA, etc.) and solvent(s) used in the composition. The comonomers of the present invention, together with the other components of the system, are preferably intended to promote penetration of the self-etching copolymerizable primer composition into the openings created by abrading or decalcifying (etching) tooth dentin and/or enamel to assist in formation of strong adherence between the self-etching primer and adhesives and the dental substrate.

It is preferred that the above described compositions provide high initial bond strengths (about 15 to 20 MPa or higher) and are stable at room temperature (e.g. at about 22° C. The compositions are preferably stable for at least about one month, at least about two months, at least about three months, at least about four months, at least about five months, at least about six months, at least about nine months, at least about one year, or at least about two years. Stability can be assayed by comparing shear bonding strengths of dentin before and after storage. A stable composition preferably maintains at least about 70% of its initial shear bonding strength. More preferably, the composition maintains at least about 75%, at least about 80%, at least about 85%, at least about 90%, at least about 95%, and ideally maintains approximately its initial shear bonding strength.

Compositions lacking water have been found to be especially stable. Solvents such as ethanol, acetone, and mixtures of ethanol and acetone can be used to prepare compositions lacking water. As used herein, compositions lacking water have less than about 1 weight percent water based on the total weight of the composition. Ideally, compositions lacking water have less than about 0.5 weight percent water, or less than about 0.1 percent water. For example, commercial absolute ethanol is described as containing 99.5% ethanol, and 0.5% water.

The above described compositions can further comprise a substantially hydrophobic co-monomer compound. A substantially hydrophobic co-monomer compound is one that is capable of being co-polymerized with the polymerizable self-etching copolymerizable monomer described above. The substantially hydrophobic co-monomer compound can preferably have a low solubility in water. It is presently preferred that the substantially hydrophobic co-monomer compound have a solubility in water of less than about three weight percent, less than about two weight percent, or less than about one weight percent. One example of such a substantially hydrophobic co-monomer compound is Bis-[2-(methacryloyloxy)ethyl]phosphate (Bis-MEP).

Specific self-etching copolymerizable primer compositions can consist essentially of or consist of 2-acrylamido-2-methylpropanesulfonate (sulfoethyl acrylamide, AMPS), Bis-[2-(methacryloyloxy)ethyl]phosphate (Bis-MEP), and ethanol; wherein the composition is stable at 22° C. for at least about two months.

The self-etching comonomers of the present invention decalcify the uncut tooth dentin and enamel substrate and remove the smear layer present on cut dentin or enamel, opening microtubules in the dentin and spaces in the enamel. Those openings may be penetrated by the self-etching copolymerizable primer composition and the applied dental adhesive bonding composition and the primer and adhesive polymerized together upon contact with a supplied self-cure initiator or upon contact with a light cure initiator and activating light source.

Preferred methods of the present invention include initially applying a thin layer of the aforesaid preferred self-etching copolymerizable primer composition to tooth dentin and/or enamel substrates as one step of a dental restorative process. The applied, self-etching primer composition is then preferably allowed to etch or decalcify uncut dentin or tooth enamel and remove the smear layer present on cut dentin or tooth enamel substrate,- opening microtubules in the dentin and spaces in the enamel, and blot-dried. Preferably a light-cure adhesive such as One Step (Registered Trademark) or One Step Plus (Registered Trademark) from Bisco, Inc., or a light-cure and self-cure adhesive such as All Bond (Registered Trademark) from Bisco, Inc., is then applied to the etched and primed tooth surface according to the manufacturer's instructions. Those openings may be penetrated by the self-etching primer and the adhesive bonding composition. A composite such as BIS-FIL (Registered Trademark) from Bisco, Inc. or other composite or other dental restorative resin, luting composite, or other component may then be applied to the self-etching primer and adhesive composition and preferably bonded to that layer by copolymerization through light-curing or self-curing according to the manufacture's instructions. It will be appreciated by those skilled in the art that the dental compositions and the methods of the present invention have significant utility in various restorative applications. For example, compositions of the invention may be used in Class I, II or III, IV, or V direct restorations and in indirect restorations such as inlays, onlays, crowns and luting techniques wherever maximum strength and convenience is desired.

The following Examples showing presently preferred embodiments of the present invention are for illustrative purposes only, and in no way should be construed as limiting the present invention.

Test Methods

Scanning Electron Microscope Techniques

The Scanning Electron Micrographs of FIGS. 1–17 were taken using SEM equipment supplied by Topcon Company, model number SM-510. The manufacturer's instructions were followed to generate the SEMs of FIGS. 1–17. The etched surfaces were rinsed with water to promote clarity of the SEM.

Bonding Strength Test Methods

The following two test methods were employed in all of the Examples and Tables to determine the shear bonding strengths of the indicated self-etching compositions on the indicated substrates.

A. Standard Dentin Shear Bond Strength Test Procedure (SSS).

(Step a). Extracted human teeth were embedded in resin discs, abraded on the facial surface with a model trimmer, and subsequently abraded with wet 600 or 320 grit SiC paper to create a flat and smooth dentin substrate for bonding. Step b-1 or b-2 was then followed as described below depending on the selected monomer.

(Step b-1). SBA-HEMA as Self-etching Monomer

The 600 grit paper was used in this case. 2–3 coats of the chosen self-etching primer composition were applied by brush to the dentin to achieve a uniform layer. The dentin surfaces were then allowed to etch for up to 15 seconds by allowing to set on the surface of the dentin or optionally with agitation with the brush. Adhesive was then applied according to step c, below.

(Step b-2). AMPS, SEMA and Bis-MEP as Self-etching Primer Monomer(s)

The 320 grit paper was used in this case. A drop of the solution containing the self-etching copolymerizable monomer(s) was dispensed into a mixing well after shaking the solution to evenly disperse the primer monomer for monomer(s) supplied in one component systems. A bottle containing Primer B (if the self-etching primer system is two component system) was shaken for 5 sec to bring the slurry to a homogenous state. A drop of Primer A was added to a mixing well and then a drop of Primer B was dispensed into the same well. The components mixed on contact (solution turns violet).

The prepared dentin surface was dried with an air syringe for about 3 seconds to remove visible moisture. A sponge pellet or brush was dipped in the well containing the single primer or mixed Primers A and B. One or two coats of the single component solution or of the mixture, an amount sufficient to cover the surface, were applied with 10 seconds agitation. The excess primer was blot dried with a fresh sponge pellet. Adhesive was then applied according to step c, below.

(Step c) The etched and primed surface was treated with 2 coats of an adhesive One-Step (Registered Trademark), One-Step (Registered Trademark) (OS+), All Bond (Registered Trademark) 2 (AB2) or other commercial adhesives identified in the following Tables. The adhesive was air dried, and light cured (LC) or self cured (SC) according to the individual manufacturer's instructions. A #5 gel cap (bonding area 0.1684 $cm^2$) or #9 gel cap (bonding area 0.04757 $cm^2$) was filled with BIS-FIL or the indicated light cure (LC) or self cure (SC) (BIS-FIL2B) composite or cement and placed on the prepared dentin surface. The excess composite was removed with a carver and light cured from 2 sides for 40 s @ 500 mW/$cm^2$ (for LC specimens) or left for 15 min @ 37° C. oven (for SC specimens). The samples were stored in DI water at 37° C. for a desired amount of time (2 hr, 24 hr, etc.) before being broken using Instron (Model 4466) with crosshead speed of 5 mm/min. Shear bond strength (SBS) was calculated in MPa by dividing the peak load by bonding area. The mean and standard deviations were calculated for five replications (N=5) for each test.

Enamel Shear Bond Test Procedure:

The shear bond strength test to enamel was determined by the above procedure with the exception that the embedded teeth were ground and sanded to expose a layer of enamel surface.

Uncut Ename

The shear bond strength test to uncut enamel was determined by the above procedure with the following modifications- the teeth were embedded shallow in the acrylic in such way that a desired enamel surface was already exposed. The enamel surface was pumiced with a pumice slurry for 5–10 seconds. The primer mixture was then applied directly to such-prepared surface according to the procedure above.

Adhesive shear bond strengths of self-etching copolymerizable primer compositions to tooth enamel were determined by the procedure used for determining dentin shear bonding strengths.

B. Bonding to Dentin (N=10) Ultradent Method (USBS)

Additional bonding tests were performed using the below-described test method using the Ultradent bonding jig according to the following procedures:

(a) Tooth Preparation.

1) Imbed human teeth with methyl methacrylate in phenolic rings or other molds of similar size with buccal or lingual aspect exposed. [Recommended mold: 1 inch×1 inch]2)R 2) Remove enamel by grinding or sanding specimen under copious amounts of water to expose an adequate dentin surface for bonding. Care should be taken to assure that the top and bottom surfaces of the specimen are parallel.

3) For final finish use 320 grit sandpaper.

(b) Bonding Procedure Using Ultradent Jig

1) Before placing the specimen into a bonding jig, etch and rinse dentin/enamel as per manufacturer's instructions. Remove the excess water, leaving dentin moist or wet as per manufacturer's instructions.

2) Apply primers and/or adhesive to specimen as per manufacturer's instructions. DO NOT LIGHT CURE AT THIS POINT.

3) Place the specimen into the bonding jig. This is accomplished by lifting the top plate of the bonding jig and positioning the specimen under the mold. Do not allow the mold to touch the specimen surface until the bond site is chosen. Lower the top plate when dentin selection has been made. Tighten the thumbnuts until they contact the disc springs and continue to tighten ½ turn.

NOTE: Over tightening will cause the mold to flex and lift off of the surface, allowing composite to escape from underneath.

4) Light cure the adhesive through the bonding mold as per manufacturer's instructions.

5) Use a small diameter (1 mm to 5 mm) non-serrated packing instrument to pack composite into the mold until the cylinder is ½ full. Do not pack composite above the 45° angle of the mold. Note: In order to preserve the bonding mold inserts, sand and polish any sharp edges of the packing instrument.

6) Light cure the composite as per manufacture's instructions.

7) To remove the bonded specimen, loosen the thumbnuts and press down on the cured composite with a packing instrument while lifting the upper plate.

8) With a razor blade, carefully clean away any excess resin or composite from around the bonded specimen. Store in 37° C. water.

(c) Testing Procedure by Ultradent Jig

1) With a razor blade, carefully remove any cured resin or composite from around the base of the bonded specimen which would hinder positioning the crosshead directly against the dentin.

2) Place the specimen into the test base clamp and tighten the thumbnuts.

3) Prior to placing the specimen under the crosshead, lower the crosshead to a position slightly below where the composite button is able to slide into the notch.

4) Incrementally raise the crosshead until the composite button is just able to slide into the notch.

5) Position the specimen so that the dentin is flush against the crosshead and the composite button is in contact with the notch.

6) Test at 1 mm/min. and record the peak load. Based on the diameter, 2.3798 mm, of the bonded specimen, 1 lb. equals 1 MPa.

EXAMPLES

Example 1

Preparation and Testing of Single Component Self-Etching Copolymerizable Composition Using SBA-HEMA, AMPS, SEMA and Bis-MEP on Both Dentin and Cut Enamel in LC Mode SBA-HEMA monomer synthesis: The SBA-HEMA monomer was prepared according to the following method. Two moles of sulfobenzoic anhydride (SBA) was weighed into a flask to which was added 2.4 moles of 2-hydroxyethylmethacrylate (HEMA) along with 15 grams of triethylamine. The mixture was stirred and heated at 70–80° C. for one hour, during which time a clear solution resulted. At this time, the infrared spectrum of the product revealed the disappearance of the anhydride absorption bands.

SA-HEMA monomer synthesis: This monomer was prepared according to the procedure used to prepare SBA-HEMA set out above, but the starting anhydride for SA-HEMA is succinic anhydride (SA). Two moles of SA and 2.4 moles of HEMA were used for the synthesis of SA-HEMA monomer according to the SBA-HEMA procedure.

The following abbreviations are used herein: SC=self cure; LC=light cure; NA=not available; N/A=not applicable; SSBS=standard shear bond strength test results; USBS=Ultradent shear bond strength results; SBS=shear bond strength.

Other compounds identified hereinafter are compounds purchased from the manufacturers indicated above or in the following list, which list also includes the abbreviations used herein to identify those compounds: acetone (ACS grade, Ashland Chemical Inc., Columbus, Ohio); ethanol (EtOH, AAPER Alcohol & Chemical Co., Columbus, Ohio); 2-Hydroxyethyl methacrylate (2-HEMA, Rohm & Haas Co.).] chlorhexidine gluconate (Xttrium Labs, Chicago, Ill.) benzalkonium chloride (Sigma-Aldrich, Milwaukee, Wis.).

Formulation of single component self-etching copolymerizable primer compositions The following method was used to prepare the self-etching copolymerizable primer compositions set out in the following Tables 1, 2, 3, 4 and 5.

Fifty grams self-etching primer compositions were prepared containing the weight percent of each component as identified in the formulations in Table 1, 2, 3, and 4 below by weighing out in grams one-half of the indicated weight percent for that component. The procedure for preparation of the composition consisted of admixing steps.

SBA-HEMA, AMPS, SEMA and Bis-MEP monomers and/or acids were combined in a 100 ml beaker in the appropriate weight (such that the total weight percentage was 100%) of solvent comprising ethanol and/or acetone and/or water, and mixed with a magnetic stir bar until all monomers dissolved (approximately one/half hour). If comonomers or other ingredients were desired in the system, they were admixed along with the monomers and stirred as indicated above.

TABLE 1

Dentin Shear Bonding Strength using SBA-HEMA as a self-etching primer monomer (SSBS, in MPa)

| wt. % SBA-HEMA | % Solvent | Other Ingredients | Adhesive Used | SBS at 2 hrs. |
|---|---|---|---|---|
| 16% | Water 84% | | One Step ® applied over 15 s with agitation | 13.14 ± 3.97 |
| 0.5% | Acetone 49.75% Water 49.75% | | One Step ® applied over 15 s | 16.36 ± 2.31 |
| 10% | Water 55% | 30% Methacrylic Acid, 5% HEMA | One Step ® applied over 30 s with agitation | 13.24 ± 6.80 |
| 2.5% | Water 95.5% | 2% SA HEMA | One Step ® applied over 15 s with agitation | 19.49 ± 4.95 |
| 2% | Water 98% | | One Step ® applied over 15 s with agitation | 19.34 ± 4.90 |

TABLE 2

Dentin Shear Bonding Strength using AMPS as a self-etching primer monomer (SSBS, in MPa)

2a. AMPS with OS and BIS-FIL system

| | AMPS (wt. %) | | | | |
|---|---|---|---|---|---|
| | 15% | 20% | 25% | 30% | 35% |
| Dentin SBS (MPa) bonding area 0.1684 cm$^2$ | 18.3 (4.3) | 19.2 (4.3) | 17.2 (2.5) | 18.5 (2.8) | 14.6 (2.5) |
| Enamel SBS (MPa) bonding area 0.03851 cm$^2$ | NA | 13.9 (4.9) | NA | 20.7 (3.7) | 21.1 (4.6) |

TABLE 2-continued

Dentin Shear Bonding Strength using AMPS as a
self-etching primer monomer (SSBS, in MPa)

2b. SBS on dentin of AMPS with other commercial bonding agents

| AMPS (wt. %) | Solo Plus (Kerr) | Single Bond (3M) |
| --- | --- | --- |
| 15% | 15.2 (1.9) | 16.3 (4.3) |
| 30% | 18.1 (3.6) | 17.2 (3.6) |

TABLE 3

Dentin Shear Bonding Strength of using SEMA as
a self-etching primer monomer (SSBS, in MPa)

SBS on dentin of SEMA with OS and BIS-FIL system

| | SEMA (wt. %) | | | | | |
| --- | --- | --- | --- | --- | --- | --- |
| | 5% | 10% | 13% | 15% | 20% | 25% |
| Dentin SBS (MPa) bonding area 0.1684 cm² | 14.7 (4.2) | 13.0 (4.0) | 11.6 (4.1) | 14.9 (5.9) | 9.1 (3.2) | 7.4 (2.8) |
| Enamel SBS (MPa) bonding area 0.03851 cm² | NA | NA | NA | NA | 1.5 (1.7) | NA |

TABLE 4

Dentin Shear Bonding Strength of AMPS and SEMA as self-etching
primer monomers (SSBS, in MPa)
SBS of AMPS and SEMA with OS and BIS-FIL system

| | AMPS (wt. %)/SEMA (wt. %) | | |
| --- | --- | --- | --- |
| | 10/10 | 15/5 | 5/15 |
| Dentin SBS (MPa) bonding area 0.1684 cm² | 20.4(1.0) | 17.8(3.2) | 19.3(2.2) |
| Enamel SBS (MPa) bonding area 0.03851 cm² | 24.0(3.3) | 22.4(5.4) | 28.6(6.2) |

TABLE 5

Dentin Shear Bonding Strength of using Bis-MEP as a self-etching
primer promoter (SSBS, in MPa)

| 50 wt. % Bis-MEP in Ethanol | Dentin bonding area 0.1684 cm² | Enamel bonding area 004757 cm² |
| --- | --- | --- |
| SSBS, in MPa | 260 (3.0) | 17.7(6.8) |

Example 2

Preparation and Testing of Two Component Self-Etching Copolymerizable Compositions Using AMPS and Bis-MEP on Dentin in Both LC and SC Mode Two component systems comprising a first Primer A solution containing a pH indicator, water and ethanol and a second Primer B solution containing self etching copolymerizable monomer compounds were prepared according to the following general methods.

Primer A:

In a beaker, place 98.985% by wt. DI water, 1.000% by wt. ethyl alcohol. Using an analytical balance weigh 0.015% by wt. Thymol blue sodium salt and add it into the beaker. Optionally, add BAC or CHXG at desired weight percentage into the same beaker. Place a magnetic stir bar in the beaker, cover the beaker to avoid evaporation of solvents, and allow stirring on a stirring plate until all the components are dissolved.

Primer B:

Add the desired weight percent of the first selected self etching copolymerizable liquid monomer, Bis-MEP, to a beaker, add the desired weight percent of absolute ethyl alcohol. Place a magnetic stir bar in the beaker, cover the beaker to avoid evaporation of solvent, and allow to stir on a stirring plate until all Bis-MEP is dissolved. Add second selected self etching copolymerizable monomer AMPS 2404 to the beaker, continue to stir until all of the components are mixed evenly. For example, in order to prepare a 38/10 composition of AMPS and Bis-MEP, place 10% by wt Bis-MEP and 52% by wt absolute ethyl alcohol in a beaker, and add a magnetic stir bar in the beaker, cover the beaker to avoid evaporation of components, and allow to stir on a stirring plate until all Bis-MEP is dissolved. Add 38% by wt AMPS into the beaker and continue stirring until all the components are mixed.

The aforementioned 38/10 AMPS/Bis-MEP and other self-etching copolymerizable compositions were applied to cut and uncut tooth dentin and enamel and investigated along with conventional 37% phosphoric acid etchant solutions for shear bond strength with a variety of commercially available light cure and self cure adhesives according to the following procedures. In the below Tables, if a Primer B is listed, the above-described Primer A was admixed before application to the indicated tooth enamel or dentin surface.

TABLE 6

Dentin SBS of self-etching primer with Primer B composition of
AMPS/Bis-MEP with OS or OS+ and BIS-FIL LC system.

6a SSBS, in MPa

| | Primer B AMPS (wt. %)/Bis-MEP (wt. %) | | | |
| --- | --- | --- | --- | --- |
| | 10/10 | 30/10 | 38/10 | 40/10 |
| Dentin SBS (MPa) bonding area 0.1684 cm2 OS | NA | NA | 23.7 (3.3) | NA |
| Dentin SBS (MPa) bonding area 0.1684 cm2 OS+ | 20.3(2.4) | 20.4(2.9) | 23.2(2.3) | 23.1(0.4) |

6b USBS, in MPa (with OS)

| | Primer B AMPS (wt. %)/Bis-MEP (wt. %) | | | Control |
| --- | --- | --- | --- | --- |
| | 30/10 | 38/10 | 40/10 | (H₃PO₄ 37%) |
| Dentin USBS (MPa) | 31.1(4.1) | 35.7(4.8) | 29.4(4.4) | 38.3(4.8) |

TABLE 7

Dentin SBS of self-etching primer with Primer B composition of 38 wt. % AMPS/10 wt. % Bis-MEP with other commercial bonding agent and BIS-FIL LC system (LC) and BIS-FIL 2B (SC) (SSBS, in MPa)

| | Adhesive | | | |
|---|---|---|---|---|
| Cure Mode | All Bond 2 | Optibond Solo Plus (Kerr) | Single Bond (3M) | Prime & Bond NT (Dentsply) |
| LC (both) | 23.1(2.1) | 19.8(3.0) | 20.7(1.8) | 13.3(3.1) |
| SC (both) | 19.5(4.9) | N/A | N/A | N/A |

TABLE 8

Long term Dentin SBS of self-etching primer of Primer B AMPS/Bis-MEP (in wt. %) with OS and BIS-FIL LC system (SSBS, in MPa)

| | Time soakin in 37° C. water | | |
|---|---|---|---|
| | 24 Hr | 1 month | 3 month |
| 37% H$_3$PO$_4$ 15s + OS | 20.4(2.7) | 20.2(2.7) | 15.2(4.8) |
| 30/10 AMPS/Bis-MEP + OS | 19.8(1.6) | 21.1(1.8) | NA |
| 43/10 AMPS/Bis-MEP + OS | 20.3(2.9) | 21.6(1.6) | NA |
| 43/27 AMPS/Bis-MEP + OS | 25.2(1.9) | 24.3(2.2) | 20.2(2.0) |
| 37% H3PO4 15s + OS | 25.2(3.9) | 19.7(2.3) | NA |
| 30/10 AMPS/Bis-MEP + OS | 21.5(3.1) | 21.7(2.2) | NA |
| 43/10 AMPS/Bis-MEP + OS+ | 23.6(3.7) | 20.8(1.7) | NA |

TABLE 9

Dentin SBS of self-etching primer with Primer B composition of AMPS/Bis-MEP with OS or OS+ and BIS-FIL 2B SC system 9a SSBS, in MPa (with OS+)

| | Component B AMPS (wt. %)/Bis-MEP (wt. %) | | |
|---|---|---|---|
| | 10/10 | 30/10 | 40/10 |
| Dentin SBS (MPa) bonding area 0.1684 cm2 OS+ | 20.3(2.4) | 20.5(1.6) | 21.8(2.4) |

9b USBS, in MPa (with OS)

| | Component B AMPS (wt. %)/Bis-MEP (wt. %) | | | |
|---|---|---|---|---|
| | 30/10 | 38/10 | 40/10 | 37% H3PO4 |
| Dentin USBS (MPa) | 35.9(3.7) | 34.8(6.0) | 32.5(4.0) | 39.8(6.0) |

TABLE 10

SC dentin SBS of self-etching primer with Primer B composition of 38 wt. % AMPS/10 wt. % Bis-MEP with OS or OS+ (SSBS, in MPa)

| | SC composite | | | | | |
|---|---|---|---|---|---|---|
| | BIS-FIL 2B | | Duolink | | C&B | |
| Etchant | 38/10 | 37% H$_3$PO$_4$ 15s | 38/10 | 37% H$_3$PO$_4$ 15s | 38/10 | 37% H$_3$PO$_4$ 15s |
| OS | 19.8 (2.1) | 20.3 (2.7) | 19.8 (2.2) | 13.3 (1.8) | 17.6 (4.1) | 16.2 (1.9) |
| OS+ | 22.1 (1.9) | 19.4 (2.3) | 18.7 (2.4) | 19.1 (2.3) | 16.6 (1.9) | 17.7 (1.9) |

TABLE 11

LC and SC Dentin SBS of self-etching primer with Primer A also containing 0.25 wt. % BAC and Primer B composition of 38 wt. % AMPS/10 wt. % Bis-MEP and with OS+ and other commercial bonding agents (SSBS, in MPa).

| | Adhesive | | | |
|---|---|---|---|---|
| | OS+ | Solo Plus Kerr | Single Bond (3M) | Prime Bond N & T (Dentsply) |
| LC | 21.8(3.3) | 22.4(2.0) | 25.7(0.9) | 12.0(2.9) |
| SC | 18.4(4.1) | N/A | N/A | N/A |

The effect of introduction of an antimicrobial agent benzalkonium chloride (BAC) or chlorhexidine gluconate (CHXG) into compositions according to the present invention was also investigated as follows: 0.5 wt. % of BAC or CHXG antimicrobial agent was added to the Primer A solutions of the two component self etching system of Example 2 wherein the second component of the both systems comprises 38–40 wt. % AMPS and 10% Bis-MEP. The shear bond strength of these compositions was evaluated according to the SBBS methods described above. The composition containing BAC exhibited a shear bond strength of 24.0 (1.6) MPa (n=4), and the bond strength was 23.2 (2.3) MPa (n=4) to tooth dentin for the composition containing chlorhexidine gluconate.

Example 3

Testing Two Component Self-Etching Copolymerizable Composition Using AMPS and Bis-MEP on Cut Enamel in LC Mode

TABLE 12

Cut enamel SBS of self-etching primer with Primer B composition of AMPS/Bis-MEP with OS or OS+ and BIS-FIL LC system 12a SSBS, in MPa

| | Primer B AMPS (wt. %)/Bis-MEP (wt. %) | | |
|---|---|---|---|
| | 30/10 | 38/10 | 40/10 |
| OS | NA | 24.7(3.1) | 24.1(2.0) |
| OS+ | 18.1(4.8) | 22.2(4.7) | 23.6(2.2) |

12b USBS, in MPa (with OS)

| | Primer B AMPS (wt. %)/Bis-MEP (wt.%) | |
|---|---|---|
| | 30/10 | 40/10 |
| Cut Enamel USBS (MPa) | 29.4(4.5) | 31.6(4.3) |

Example 4

Testing Two Component Self-Etching Copolymerizable Composition Using AMPS and Bis-MEP on Uncut Enamel in LC Mode The SBS of 38 wt. % AMPS/10 wt. % Bis-MEP on uncut enamel was also evaluated. The following results were observed.

TABLE 13

Uncut enamel SBS of self-etching primer with Primer B composition of AMPS/Bis-MEP with OS or OS+ and BIS-FIL LC system

|  | AMPS/Bis-MEP 38/10 | 37% H$_3$PO$_4$ 15 sec |
|---|---|---|
| OS | 19.7(4.5) | 20.7(4.9) |
| OS+ | 19.0(2.0) | 20.9(4.9) |

Example 5

Testing AMPS/Bis-MEP (38/10 wt. %), SE Bond and Prompt L-Pop on Dentin and Enamel in LC and SC Modes The ability of AMPS/Bis-MEP primer systems and two commercial priming systems to bond to tooth substrates was also evaluated. SE Bond and Prompt L-Pop were applied to cut and uncut enamel and to dentin according to the manufacturer's instructions, except that no acid etching step of enamel was performed, and curing was done as set out in Table 14. The following results were observed.

TABLE 14

SSBS of SE Bond and Prompt L-Pop on dentin and cut enamel

14a SSBS, in MPa

|  | Dentin LC | Dentin SC (with BIS-FIL 2B) | Cut Enamel LC | Uncut Enamel SC |
|---|---|---|---|---|
| SE Bond | 20.9(0.8) | N/A | 18.5(3.0) | N/A |
| Prompt L-Pop | 17.9(1.6) | N/A | NA | N/A |
| 37% H$_3$PO$_4$ 15s + OS | 22.6(1.8) | 20.3(2.7) | 24.9(4.1) | 20.7(4.9) |
| Primer B 38/10 AMPS/Bis-MEP + OS | 23.7(3.3) | 19.8(2.1) | 24.7(3.1) | 19.7(4.5) |

14b USBS, in MPa

|  | Dentin LC | Dentin SC (with BIS-FIL 2B) | Cut Enamel |
|---|---|---|---|
| SE Bond | 29.4(11.7) | N/A | NA |
| Prompt L-Pop | 12.5(4.4) | N/A | NA |
| 37% H$_3$PO$_4$ 15s + Os | 38.3(4.8) | 39.8(6.0) | NA |
| Primer B 38/10 AMPS/Bis-MEP + OS | 35.7(4.8) | 34.8(6.0) | 24.7(3.1) |

It is expected that other commercial adhesives and composites will also function well with applicant's self-etching copolymerizable primer compositions and methods. Utilization of self-etching primer compositions according to the present invention provide bonding strength comparable or greater than that provided by conventional acid etchants without the need for a separate rinse step, and do so in both self-cure and light cure environments.

The compositions using the AMPS/Bis-MEP Primer B self-etching primers in one container and a separate Primer A component including water and ethanol in another container according to the present invention exhibited good stability, when stored at room temperature for many months and at elevated temperature (37° C. for at least four months, they still provided good bond strengths after admixture and application. The self-etching copolymerizable compositions according to the present invention also yielded excellent bonding results for all the substrates tested.

As shown in the accompanying Figures, self-etching copolymerizable primers of the present invention provide etching of both cut and uncut dentin and enamel surfaces to a degree comparable to that of conventional acid etchants.

For example, and as shown in FIGS. 1–2, there is significant decalcification of the cut unetched dentin substrate (FIG. 1) when conventional phosphoric acid solution is applied thereto and rinsed away (FIG. 2) and when the self-etching primers of the present invention are applied and rinsed to permit clear SEM images (FIGS. 3–4.). Unetched enamel is shown in FIG. 5 after sanding and in FIG. 9 after pumicing, two conventional abrasion techniques. The self-etching primers according to the present invention etched both abraded surfaces to a degree comparable to that provided by conventional acid etchant, 37% phosphoric acid. (Compare FIG. 6 vs. FIGS. 7–8 and FIG. 10 vs. FIGS. 11–13. The self-etching primers of the present invention (FIGS. 16–17) also etch cut enamel to a degree comparable to that provided by conventional acid etchant (compare with FIGS. 14 burr cut enamel) and conventional acid etched burr cut enamel (FIG. 15).

As shown by the foregoing Examples, compositions and methods according to the present invention simplify the overall restorative process while providing high bond strengths and stable, storable compositions or components. Simplification and significant time savings are realized through formulation of applicants' self-etching copolymerizable primer component(s)—well in advance of use of such component(s) in compositions on the patient. Such advance formulation can be undertaken by the manufacturer at the plant due to the considerable shelf life of applicants' components.

It is also contemplated that the advantages inherent in applicants' compositions and methods can be realized by formulating applicants' compositions in one or two component parts and in placing those parts into kits containing one or two separate containers, the contents of which could be admixed by the dental professional in his or her office. The advantages of simplification and expeditious patient treatment could be realized by the manufacturer supplying the one or two container formulations in amounts whereby their admixture can be conducted in amounts sufficient to treat two or more restorations on a given patient. Treatment time can be minimized because such use of such compositions does not require a separate rinsing step or the application of a separate bonding resin before application of the dental adhesive required by other commercial products. A third component comprising a dental adhesive could also be supplied in the kit.

As indicated above and in the foregoing Examples, components according to the present invention are both "self-etching" and "self-stable", i.e. they exhibit high bond strengths over at least about four months storage at elevated temperatures, which is expected to translate into even longer stability at room temperature. Such enhanced stability permits pre-formulation of the self-etching copolymerizable components of applicants' compositions and their use in applicants' claimed methods. Compositions and methods of the present invention may also be used in indirect procedures, such as the seating of inlays, onlays and crowns in which self curing catalysts may be a necessity, as well as direct restorations involving light curing or self curing, permitting the dental professional to choose the best curing procedure for the clinical picture. Compositions according to the present invention also lessen or eliminate polymerization inhibition exemplified by poor bond strength found in commercial self-etch systems seeking to employ self-cure protocols. Compositions and methods of the present invention are also contemplated wherein only one or two coatings are necessary to apply the composition to the tooth enamel and/or dentin substrate and adequately etch, prime and impart improved adhesion to such substrates, saving further patient time and professional time and effort.

Example 6

Solubility Testing of Bis-MEP

Several experiments were performed to evaluate the solubility of Bis-MEP in various solvent systems. Bis-MEP (3.00 g, 14.72 weight percent), ethanol (7.01 g, 34.40 weight percent), and water (10.37 g, 50.88 weight percent) produced a clear solution at room temperature.

Mixtures of 20 weight percent and 10 weight percent Bis-MEP in water (no ethanol) were not homogeneous. The mixtures contained an oily layer at the bottom, and a cloudy white layer at the top of the container. A 2 weight percent mixture in water did not dissolve, and formed large, oily spots. Adding additional water until the concentration of Bis-MEP was 0.67 weight percent did not dissolve the material. Accordingly, the solubility of Bis-MEP in water is less than 0.67 weight percent.

Example 7

Evaluation of NanoBond Material

A sample of commercially available NanoBond primer was obtained. NanoBond is sold by Jeneric/Pentron, Inc., and is believed to contain AMPS, a hydrophilic monomer believed to be HEMA, and water, as described in U.S. Patent Application Publication 2000/0019456 A1. The sample was stored at room temperature for one month prior to testing.

Six specimens were prepared using dentin as a substrate, according to the manufacturer's suggested methods for LC and Bisfil All Purpose. Etching was performed using 320 grit paper. The specimens were prepared and tested according to Test Method A, described earlier. The following Instron and shear bonding strength results were obtained using a bond area of 0.1684 cm$^2$.

TABLE 15

NanoBond test results

| Specimen | Instron reading (kg) | SBS (psi) | SBS (MPa) |
|---|---|---|---|
| 1 | 28.3 | 2389 | 16.48 |
| 2 | 4.7 | 398.9 | 2.75 |
| 3 | 9.0 | 761.4 | 5.25 |
| 4 | 4.6 | 387.6 | 2.67 |
| 5 | 34.7 | 2932.6 | 20.23 |
| 6 | 30.5 | 2572.2 | 17.74 |
| Average | 18.6 | 1573.6 | 10.85 |
| Std. Dev. | 14.0 | 1179.4 | 8.13 |
| Co. Var. % | 74.9 | 74.9 | 74.9 |

The values obtained for the six specimens varied widely. In half of the specimens, the SBS was very low, effectively not bonding to the material. A repeat of this experiment using NanoBond stored for six months gave an average SBS of 4.85 MPa, approximately half of the average value obtained after one month storage.

An additional test was performed using a drybonding technique with NanoBond. The substrate was Dentin 2×, and the bond area was 0.1521 cm$^2$. The NanoBond was about six months old at the time of testing.

TABLE 16

NanoBond test results from dry bonding

| Specimen | Instron reading (kg) | SBS (psi) | SBS (MPa) |
|---|---|---|---|
| 1 | 13.4 | 1132.9 | 7.81 |
| 2 | 27.9 | 2356.9 | 16.25 |
| 3 | 27.8 | 2345.9 | 16.18 |
| 4 | 2.6 | 219.8 | 1.52 |
| 5 | 1.0 | 88.4 | 0.61 |
| Average | 14.6 | 1228.8 | 8.47 |
| Std. Dev. | 13.0 | 1101.0 | 7.59 |
| Co. Var. % | 89.6 | 89.6 | 89.6 |

As before, considerable variation in the results were observed. Two of the five specimens did not effectively bond. Fractures were observed in specimens 2 and 3. This experiment was repeated to determine the reproducibility of the results.

TABLE 16

NanoBond test results from dry bonding

| Specimen | Instron reading (kg) | SBS (psi) | SBS (MPa) |
|---|---|---|---|
| 1 | 9.9 | 838.5 | 5.78 |
| 2 | 6.1 | 519.0 | 3.58 |
| 3 | 8.2 | 695.8 | 4.80 |
| 4 | 15.0 | 1268.8 | 8.75 |
| 5 | 2.3 | 197.2 | 1.36 |
| Average | 8.3 | 703.9 | 4.85 |
| Std. Dev. | 4.7 | 386.3 | 2.73 |
| Co. Var. % | 56.3 | 56.3 | 56.3 |

Again, the results obtained varied widely. While none of the SBS values were as low as specimen 5 from the previous experiment, none were as high as specimens 2 and 3 either.

The commercial NanoBond product does not appear to produce reproducible bond strengths, and rapidly loses its efficacy upon storage.

Formulations of other stable self etching primer and adhesive bonding compositions according to the present invention will also be apparent to those skilled in the art in view of applicants' disclosure of their presently preferred compositions and presently preferred methods. Those of skill in the art will also appreciate that applicants' preferred solvents may include combinations of various concentrations of other well-known solvents which are appropriate for the monomers and acids of the present invention, such as water and other volatile solvents, together with or possibly in place of some or all of applicants' presently preferred ethanol, water, and/or acetone solvents. The foregoing detailed description has been given for clarity of understanding only, and no unnecessary limitations should be understood there from, as modifications there from will be apparent to those skilled in the art.

What is claimed is:

1. A self-etching copolymerizable primer composition consisting essentially of:
2-acrylamido-2-methylpropanesulfonate;
Bis-[2-(methacryloyloxy)ethyl]phosphate; and
ethanol;
wherein the composition is stable at 22° C. for at least about two months.

2. A self-etching copolymerizable primer composition consisting of:
2-acrylamido-2-methylpropanesulfonate;
Bis-[2-(methacryloyloxy)ethyl]phosphate; and
ethanol;
wherein the composition is stable at 22° C. for at least about two months.

* * * * *